US00PP33849P2

(12) United States Plant Patent
Heuger

(10) Patent No.: US PP33,849 P2
(45) Date of Patent: Jan. 11, 2022

(54) ***SAXIFRAGA* PLANT NAMED 'SH 1911'**

(50) Latin Name: *Saxifraga cortusifolia*
Varietal Denomination: SH 1911

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 17/178,003

(22) Filed: Feb. 17, 2021

(51) Int. Cl.
*A01H 5/02* (2018.01)
*A01H 6/80* (2018.01)

(52) U.S. Cl.
USPC ..... Plt./263.1
CPC ..... *A01H 6/80* (2018.05)

(58) Field of Classification Search
USPC ..... Plt./263.1
CPC ..... A01H 6/80
See application file for complete search history.

(56) References Cited

PUBLICATIONS

UPOV hit on *Saxifraga* plant named 'SH 1911', QZ PBR 2020/0511, filed Feb. 18, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Saxifraga* plant named 'SH 1911', characterized by its upright to outwardly spreading and mounded plant habit; moderately vigorous growth habit; leaves that have dark green-colored upper surfaces and greyed purple-colored lower surfaces; and numerous bright white-colored flowers held about the foliar plane.

2 Drawing Sheets

Figure 1:
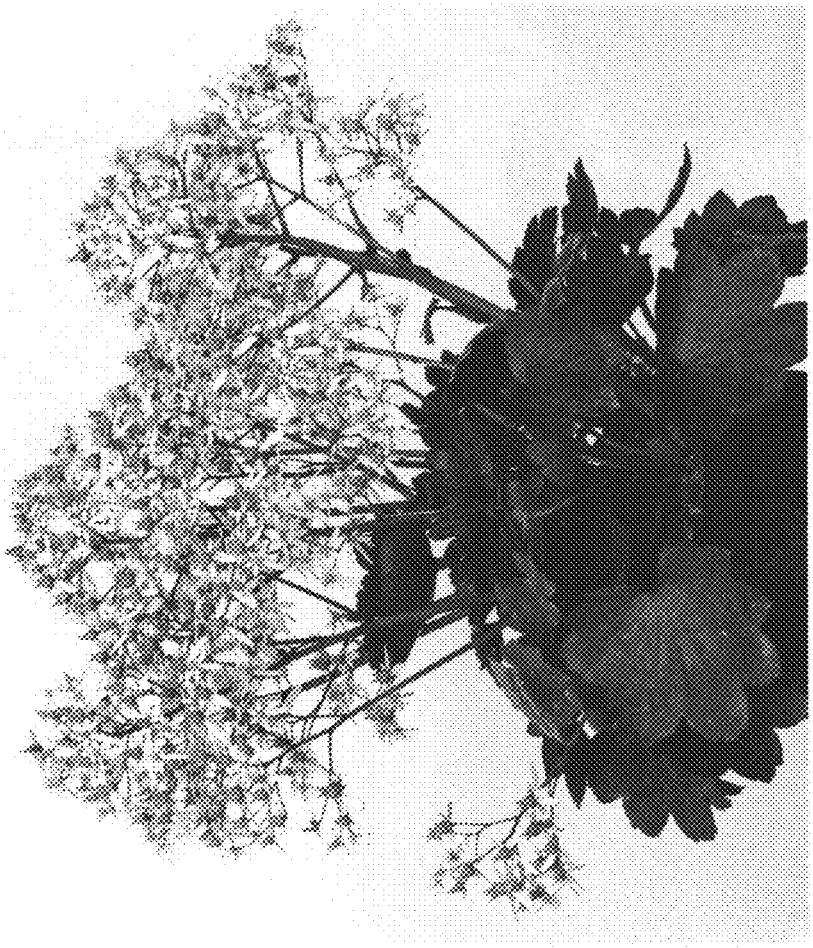

Botanical designation: *Saxifraga cortusifolia.*
Cultivar denomination: 'SH 1911'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Feb. 18, 2020, application number 2020/0511. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Saxifraga* plant, botanically known as *Saxifraga cortusifolia* and hereinafter referred to by the name 'SH 1911'.

The new *Saxifraga* plant is a product of a planned breeding program conducted by the Inventor in Glandorf, Germany. The objective of the breeding program was to create new uniform *Saxifraga* plants with unique and attractive plant habit, leaf and flower coloration.

The new *Saxifraga* plant originated from a cross-pollination conducted by the Inventor in Glandorf, Germany in October, 2013 of a proprietary selection of *Saxifraga cortusifolia* identified as code number 2013-44, not patented, as the female, or seed patent and a proprietary selection of *Saxifraga cortusifolia* identified as code number 2013-459, not patented, as the male, or pollen parent. The new *Saxifraga* plant was discovered and selected by the Inventor as a single flowering plant from within the progeny of the stated cross-pollination grown in a controlled greenhouse environment in Glandorf, Germany in September, 2014.

Asexual reproduction of the new *Saxifraga* plant by in vitro axillary meristem culture in a controlled environment in Glandorf, Germany since May, 2015 has shown that the unique features of this new *Saxifraga* plant are stable and reproduced true to type in successive generations.

SUMMARY OF THE INVENTION

Plants of the new *Saxifraga* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SH 1911'. These characteristics in combination distinguish 'SH 1911' as a new and distinct *Saxifraga* plant:

1. Upright to outwardly spreading and mounded plant habit.
2. Moderately vigorous growth habit.
3. Leaves that have dark green-colored upper surfaces and greyed purple-colored lower surfaces.
4. Freely flowering habit.
5. Bright white-colored flowers held above the foliar plane.

Plants of the new *Saxifraga* differ from plants of the female parent selection in the following characteristics:

1. Upper surfaces of leaves of plants of the new *Saxifraga* are lighter green in color than the upper surfaces of leaves of plants of the female parent selection.
2. Flowers of plants of the new *Saxifraga* are bright white in color whereas flowers of plants of the female parent selection are creamy white in color.

Plants of the new *Saxifraga* differ from plants of the male parent selection in the following characteristics:

1. Upper surfaces of leaves of plants of the new *Saxifraga* are dark green in color whereas upper surfaces of leaves of plants of the male parent selection are red in color.
2. Flowers of plants of the new *Saxifraga* are brighter white in color than flowers of plants of the male parent selection.

Plants of the new *Saxifraga* can be compared to plants of *Saxifraga cortusifolia* 'SH 1925', not patented. Plants of the new *Saxifraga* differ primarily from plants of 'SH 1925' in the following characteristics:

1. Upper surfaces of leaves of plants of the new *Saxifraga* are lighter green in color than the upper surfaces of leaves of plants of 'SH 1925'.
2. Flowers of plants of the new *Saxifraga* are bright white in color whereas flowers of plants of 'SH 1925' are pink in color.

BRIEF DESCRIPTION OF THE PHOTOGRAPHS

The accompanying colored photographs illustrate the overall appearance of the new *Saxifraga* plant showing the colors as true as it is reasonably possible to obtain in colored reproductions of this type. Colors in the photographs may differ slightly from the color values cited in the detailed botanical description which accurately describe the colors of the new *Saxifraga* plant.

The photograph on the first sheet (FIG. 1) is a side perspective view of a typical flowering plant of 'SH 1911' grown in a container.

Figure 2:
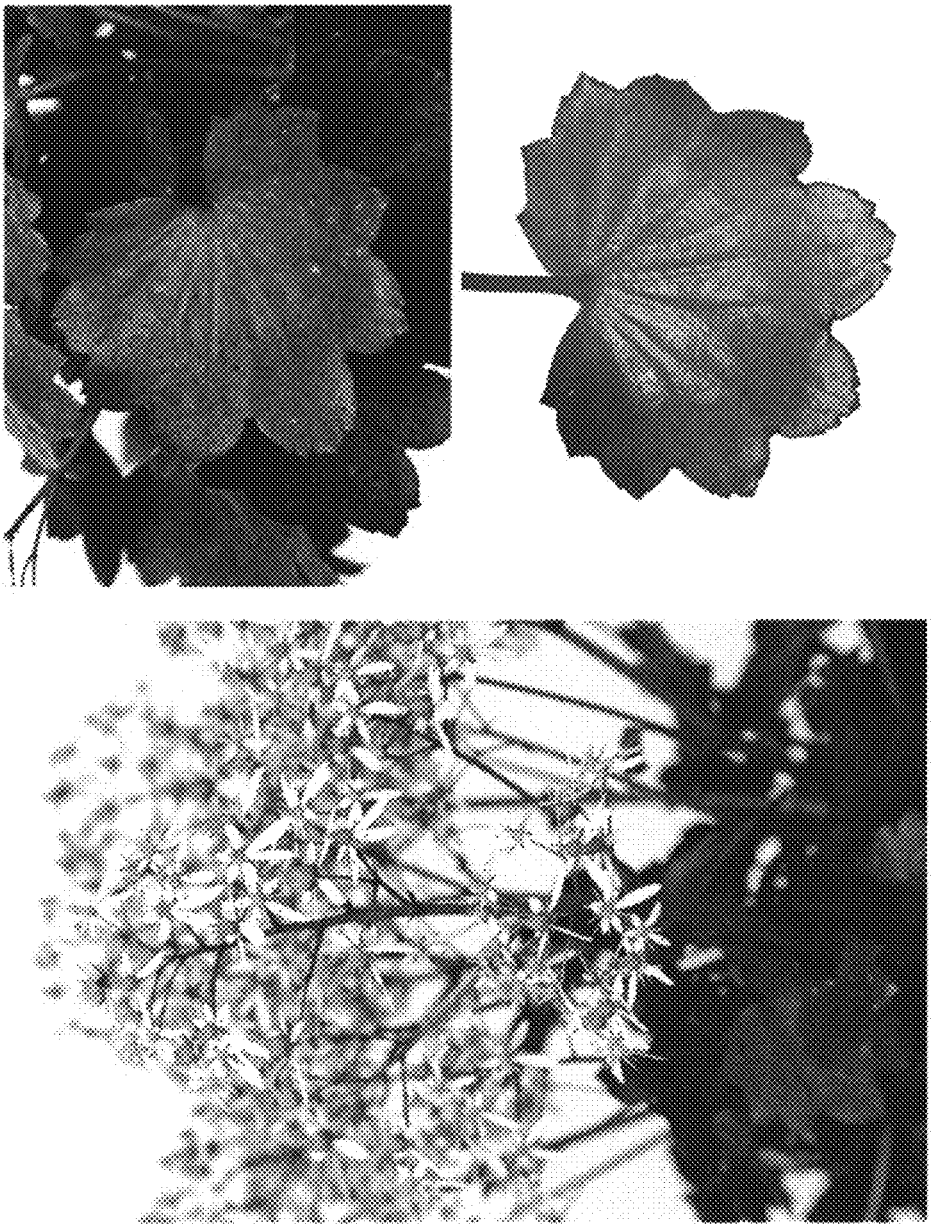

The photograph on the second sheet (FIG. 2) is a close-up view of a typical flowering plant of 'SH 1911'.

DETAILED BOTANICAL DESCRIPTION

The aforementioned photographs and following observations, measurements and values describe plants grown during the summer and autumn in 10.5-cm containers in a glass-covered greenhouse in Glandorf, Germany and under cultural practices typical of commercial *Saxifraga* production. During the production of the plants, day temperatures ranged from 18° C. to 28° C. and night temperatures ranged from 14° C. to 20° C. Plants were six months old when the photographs and the description were taken. In the following description, color references are made to The Royal Horticultural Society Colour Chart, 2015 Edition, except where general terms of ordinary dictionary significance are used.

Botanical classification: *Saxifraga cortusifolia* 'SH 1911'.

Parentage:

*Female, or seed, parent*.—Proprietary selection of *Saxifraga cortusifolia* disclosed as code number 2013-44, not patented.

*Male, or pollen, parent*.—Proprietary selection of *Saxifraga cortusifolia* disclosed as code number 2013-459, not patented.

Propagation:

*Type*.—In vitro axillary meristem culture.

*Time to produce a rooted young plant in vitro*.—About 36 to 42 days at temperatures about 22° C. to 24° C.

*Root description*.—Fine, fibrous; typically white to brown in color, actual color of the roots is dependent on substrate composition, water quality, fertilizer type and formulation, substrate temperature and physiological age of roots.

*Rooting habit*.—Moderately freely branching; sparse to medium density.

Plant description:

*Plant and growth habit*.—Herbaceous perennial; upright to outwardly spreading and mounding plant habit with flowers held above the foliar plane; overall plant shape, broadly inverted triangular; moderately vigorous growth habit and moderate growth rate.

*Plant height, soil level to top of foliar plane*.—About 11.1 cm.

*Plant height, soil level to top of floral plane*.—About 24 cm.

*Plant diameter* (*area of spread*).—About 24.8 cm.

Leaf description:

*Arrangement*.—Leaves arranged in a basal rosette; alternate and single.

*Length*.—About 5.5 cm.

*Width*.—About 7.1 cm.

*Shape*.—Reniform in outline.

*Apex*.—Abruptly acute.

*Base*.—Deeply truncate to hastate, lobes free.

*Margin*.—Serrate and palmately lobed with about nine lobes per leaf; sinuses shallow to medium in depth and convergent.

*Texture and luster, upper surface*.—Moderately pubescent; slightly glossy.

*Texture and luster, lower surface*.—Sparsely pubescent; moderately glossy.

*Venation pattern*.—Pinnate.

*Color*.—Developing leaves, upper surface: Close to 147A; lobes tinged with close to 181A. Developing leaves, lower surface: Close to between 60C and N77B; towards the margins, close to 177A. Fully developed leaves, upper surface: Close to between NN137A and 147A; distal lobes, tinged with close to 200A; venation, close to between NN137A and 147A occasionally tinged with close to N200A. Fully developed leaves, lower surface: Close to between N77B and 186A; distal lobes, tinged with close to 187C; venation, close to 197B.

*Petioles*.—Length: About 8.5 cm. Diameter: About 3 mm. Strength: Weak. Texture and luster, upper and lower surfaces: Mostly smooth, glabrous and distally sparsely pubescent; slightly glossy. Color, upper and lower surfaces: Close to 183B to 183C.

*Stipules*.—Arrangement: Two at the base of the petiole. Length: About 1.9 cm. Diameter: About 5 mm. Color, upper surface: Close to 182B. Color, lower surface: Close to 185C.

Flower description:

*Flower shape and habit*.—Rotate flowers arranged in terminal compound corymbs; freely flowering habit with about 100 flowers per inflorescence and about 1,000 flowers developing per plant; flowers face mostly upright to slightly outwardly.

*Fragrance*.—None detected.

*Natural flowering season*.—Plants begin flowering about six months after planting; plants flower naturally from the late summer into the winter in Germany.

*Flower longevity on the plant*.—About two weeks; flowers persistent.

*Flower buds*.—Length: About 1 mm. Diameter: About 1.5 mm. Shape: Flattened globular. Texture and luster: Smooth, glabrous; matte. Color: Close to 182A.

*Inflorescence height* (*including peduncle*).—About 22.7 cm.

*Inflorescence diameter*.—About 12 cm.

*Flower diameter*.—About 1.2 cm by 1.5 cm.

*Flower depth* (*height*).—About 6 mm.

*Petals*.—Quantity and arrangement: About five, occasionally six, arranged in a single whorl; upper three or four petals are smaller than lower one or two petals. Length, upper petals: About 5 mm to 7 mm. Width, upper petals: About 2 mm to 3 mm. Length, lower petals: About 1.1 cm to 1.3 cm. Width, lower petals: About 2.5 mm to 4 mm. Shape, upper petals: Ovate. Shape, lower petals: Oblanceolate to elliptic. Apex, upper petals: Bluntly acute to obtuse. Apex, lower petals: Bluntly acute to obtuse to occasionally emarginate. Base, upper and lower petals: Attenuate. Margin, upper petals: Entire; not undulate. Margin, lower petals: Mostly entire, occasionally sparsely serrate; not undulate. Texture and luster, upper and lower petals, upper and lower surfaces: Smooth, glabrous; slightly velvety; matte. Color, upper and lower petals: When opening, upper and lower surfaces: Close to 157C. Fully opened, upper surface: Close to 157B; venation, close to 157B; with development, color becoming closer to 157A. Fully opened, lower surface: Close to 157B; venation, close to 157B; with development, color becoming closer to between 145D and 157B.

*Sepals*.—Quantity and arrangement: Five, arranged in a single whorl. Length: About 3 mm. Width: About 1 mm. Shape: Oblong. Apex: Bluntly acute. Base: Cuneate. Margin: Entire. Texture and luster, upper surface: Smooth, glabrous; matte. Texture and luster, lower surface: Smooth, glabrous; slightly glossy. Color: When opening, upper surface: Close to N148C; towards the margins and apex, close to 182B. When opening, lower surface: Close to N148D tinged with close to 184C. Fully opened, upper surface: Close to N148B; towards the margins and apex, close to 182B. Fully opened, lower surface: Close to N148D tinged with close to 184C.

*Peduncles*.—Length: About 21 cm. Diameter: About 3 mm. Aspect: About 15° from vertical; secondary peduncles, about 35° from main peduncle axis. Strength: Moderately weak. Texture and luster: Smooth, glabrous; glossy. Color: Close to 174A.

*Pedicels*.—Length: About 1.1 cm. Diameter: About 0.5 mm. Aspect: About 35° from peduncle axis. Strength: Moderately strong. Texture and luster: Sparsely to moderately pubescent; slightly glossy. Color: Close to 148A to 148B.

*Reproductive organs*.—Stamens: Quantity per flower: About twelve. Filament length: About 4 mm. Filament color: Close to NN155D. Anther shape: Double reniform. Anther size: About 0.5 mm by 0.6 mm. Anther color: Close to N77B. Pollen amount: Moderate. Pollen color: Close to 29B. Pistils: Quantity per flower: About three, occasionally two. Pistil length: About 2.5 mm. Stigma diameter: About 0.2 mm. Stigma shape: Club-shaped. Stigma color: Close to 145D. Style length: About 2.3 mm. Style color: Close to 145A. Ovary color: Close to N144A. Floral bracts: Quantity per flower: One. Length: About 1.3 cm. Diameter: About 4 mm. Shape: Ovate. Apex: Acute. Base: Broadly cuneate. Color, upper surface: Close to 147A; towards the base, close to 183B. Color, lower surface: Close to 183A. Seeds and fruits: To date, seed and fruit development have not been observed on plants of the new *Saxifraga*.

Temperature tolerance: Plants of the new *Saxifraga* have been observed to tolerate temperatures ranging from about −7° C. to about 35° C. and to be suitable for USDA Hardiness Zones 8b through 11.

Pathogen & pest resistance: To date, plants of the new *Saxifraga* have not been observed to be resistant to pathogens and pests common to *Saxifraga* plants.

It is claimed:

1. A new and distinct *Saxifraga* plant named 'SH 1911' as illustrated and described.

* * * * *